United States Patent [19]

Falk et al.

[11] Patent Number: 5,312,852
[45] Date of Patent: May 17, 1994

[54] 2-(2-HYDROXY-3-PERFLUOROALKYLTHIOMETHYL-5-ALKYLPHENYL)-2H-BENZOTRIAZOLES, PROCESSES FOR PREPARING THEM AND STABILIZED COMPOSITIONS THEREOF

[75] Inventors: Robert A. Falk, New City; Gregory R. Coughlin, Poughkeepsie, both of N.Y.

[73] Assignee: Ciba-Geigy Corporation, Ardsley, N.Y.

[21] Appl. No.: 90,834

[22] Filed: Jul. 12, 1993

Related U.S. Application Data

[62] Division of Ser. No. 926,105, Aug. 5, 1992, Pat. No. 5,250,698.

[51] Int. Cl.$^5$ .................. C08K 5/3475; C07D 249/20
[52] U.S. Cl. ..................... 524/91; 252/402; 548/256; 548/260
[58] Field of Search .......... 252/402; 524/91; 548/256, 260

[56] References Cited

U.S. PATENT DOCUMENTS

| | | | |
|---|---|---|---|
| 2,965,659 | 12/1960 | Tiers | 260/408 |
| 2,972,638 | 2/1961 | Tiers | 260/653.1 |
| 3,004,896 | 10/1961 | Heller et al. | 167/90 |
| 3,055,896 | 9/1962 | Boyle et al. | 260/249.5 |
| 3,072,585 | 1/1963 | Milionis et al. | 260/22 |
| 3,074,910 | 1/1963 | Dickson, Jr. | 260/45.75 |
| 3,088,849 | 5/1963 | Friedlander | 117/127 |
| 3,145,222 | 8/1964 | Brace | 260/408 |
| 3,189,615 | 6/1965 | Heller et al. | 260/308 |
| 3,230,194 | 1/1966 | Boyle | 260/45.8 |
| 3,544,663 | 12/1970 | Hauptscheir et al. | 260/900 |
| 3,655,732 | 4/1972 | Rondestvedt, Jr. | 260/486 H |
| 3,766,205 | 10/1973 | Heller et al. | 548/260 |
| 4,127,586 | 11/1978 | Rolly et al. | 260/308 B |
| 4,226,763 | 10/1980 | Dexter et al. | 260/458 N |
| 4,278,590 | 7/1981 | Dexter et al. | 260/45.8 N T |
| 4,278,589 | 7/1981 | Dexter et al. | 260/458 N T |
| 4,283,327 | 8/1981 | Dexter et al. | 260/45.8 N T |
| 4,383,863 | 5/1983 | Dexter et al. | 106/125 |
| 4,584,143 | 4/1986 | Falk | 558/240 |
| 4,675,352 | 6/1987 | Winter et al. | 524/91 |
| 4,681,905 | 7/1987 | Rubota et al. | 524/91 |
| 4,788,292 | 11/1988 | Clark et al. | 548/260 |
| 4,853,471 | 8/1989 | Rody et al. | 548/261 |

OTHER PUBLICATIONS

C.A. vol. 77, 1972 153215p.
C.A. vol. 77, 1972 34535h.
C.A. vol. 79, 1973 115594v.

*Primary Examiner*—Kriellion S. Morgan
*Attorney, Agent, or Firm*—Luther A. R. Hall

[57] ABSTRACT

2-(2-Hydroxy-3-perfluoroalkylthiomethyl-5-alkylphenyl)-2H-benzotriazoles are prepared by reacting the Mannich base hydrohalide or quaternary salt of a 2-(2-hydroxy-5-alkylphenyl)-2H-benzotriazole with a perfluoroalkyl mercaptan. The products exhibit outstanding efficacy in protecting organic substrates from light induced deterioration as well as good resistance to loss by volatilization or exudation during the processing of stabilized compositions at elevated temperatures.

13 Claims, No Drawings

2-(2-HYDROXY-3-PERFLUOROALKYLTHI- OMETHYL-5-ALKYLPHENYL)-2H-BENZO- TRIAZOLES, PROCESSES FOR PREPARING THEM AND STABILIZED COMPOSITIONS THEREOF

This is a divisional of Ser. No. 07/926,105, filed Aug. 5, 1992 now U.S. Pat. No. 5,250,698.

The instant invention pertains to new 2H-benzotriazoles UV-absorbers which contain a perfluoroalkyl moiety which exhibit excellent absorption characteristics, low volatility and the ability to migrate to and to protect the polymer/air interface.

BACKGROUND OF THE INVENTION

Fluorochemical additives have demonstrated the unique ability to modify the surface properties of polymers by adsorption at the polymer/air interface even when used at very low levels. Fluorochemicals can inherently retain these unique migrating properties while maintaining the high molecular weight necessary to minimize volatility.

The UV-absorbers of the o-hydroxyphenyl-2H-benzotriazole class have long been known as effective light stabilizers for organic materials and have enjoyed considerable commercial success.

The description, preparation and uses of these valuable 2-aryl-2H-benzotriazoles are further taught in U.S. Pat. Nos. 4,383,863; 4,853,471; 4,681,905; 3,004,896; 3,055,896; 3,072,585; 4,226,763; 4,278,589; 4,675,352; 3,189,615; 3,230,194; 4,127,586 and 3,074,910.

The hitherto known 2-aryl-2H-benzotriazoles of this group have in some circumstances exhibited limited compatibility in certain substrates, and excessive tendency to exude, sublime and and/or volatilize during processing of stabilized compositions into sheets, films, fibers or other pellicles when such processing must be done at elevated temperatures. Likewise such benzotriazoles may also suffer undue loss by volatilization or sublimation from thin films or coatings, especially when subjected to elevated temperatures during use.

Attempts have been made to increase compatibility and to reduce volatilization loss by modifying the structure of the benzotriazoles. In U.S. Pat. No. 3,230,194, a higher alkyl group was substituted for methyl, and the latter compound 2-(2-hydroxy-5-tert-octylphenyl)-2H-benzotriazole exhibited superior compatibility and performance in polyethylene.

In U.S. Pat. Nos. 4,283,327; 4,278,590 and 4,383,863 there is described 2-(2-hydroxy-3,5-di-tert-octyl-phenyl)-2H-benzotriazole which exhibits an excellent combination of compatibility with and/or solubility in numerous polymeric substrates along with superior resistance to loss from stabilized compositions during high temperature processing, in end-use applications where coatings or films of the stabilized compositions are exposed to ambient weathering and light exposures, and in photographic applications.

In U.S. Pat. No. 4,675,352 liquid benzotriazoles of low volatility are prepared by alkylation of 2-(2-hydroxy-5-methylphenyl)-2H-benzotriazoles.

The foregoing non-fluorine containing 2-aryl-2H-benzotriazoles have not had the ability to migrate to and to protect a polymer/air interface.

In Kobunshi Ronbunshu 47, (5), 361–70 (1990) data are reported on an improvement in U.V. stabilization by the incorporation of vinylic benzotriazoles as comonomers with perfluoroalkyl monomers. The resultant polymeric U.V. stabilizers are effective in polystyrene possibly due to the surface accumulation of surface-active segments.

U.S. Pat. No. 4,788,292 describes perfluoroalkyl substituted 1-H- and 2H-benzotriazoles which do not contain the 2-(2-hydroxyphenyl) moiety.

Certain perfluoroalkyl-phenolic benzotriazoles are reported in JP 72/011074; 72/015210; 72/043949 and 73/026012. These substituted benzotriazoles are prepared from fluorinated triazole precursors which makes them inherently expensive and not commercialy viable. They are suggested for the improvement in stability of the polymer matrix surrounding encapsulated liquid crystals.

The instant 2-(2-hydroxy-3-perfluoroalkylthiomethyl-5-alkylphenyl)-2H-benzotriazoles are easily prepared from commercially available 2-(2-hydroxy-5-alkylphenyl)-2H-benzotriazoles. Further, in the instant benzotriazoles the pendant perfluoroalkyl chains are connected by a flexible sulfur atom to the remainder of the molecule, thus providing a more mobile perfluoroalkyl function, with improved solubility.

The subject benzotriazoles exhibit excellent absorption characteristics in the ultraviolet range, low volatility, and the ability to migrate to and protect a polymer/air interface. Their photographic inertness is particularly useful in photographic compositions, especially in protecting color dye images against the harmful effects of ultraviolet light.

DETAILED DISCLOSURE

This invention pertains to 2-(2-hydroxy-3-perfluoroalkylthiomethyl-5-alkylphenyl)-2H-benzotriazole UV absorbers and to organic materials, both polymeric and non-polymeric, stabilized thereby, as well as to stabilized compositions containing said materials. The stabilized compositions include photographic elements, plastics, coatings, fibers, and films.

More particularly, the instant invention pertains to compounds, suitable for stabilizing organic materials against light-induced deterioration, of formula I

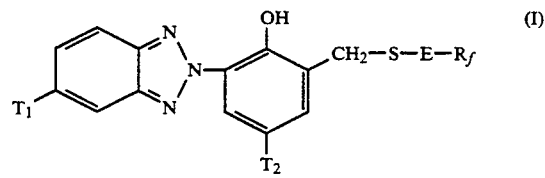

wherein $T_1$ is hydrogen, halogen, alkyl of 1 to 4 carbon atoms or alkoxy of 1 to 4 carbon atoms, $T_2$ is alkyl of 1 to 18 carbon atoms, cycloalkyl of 5 to 12 carbon atoms or phenylalkyl of 7 to 15 carbon atoms, E is a branched or straight chain alkylene of 1 to 10 carbon atoms or said alkylene interrupted by one to three groups selected from the group consisting of —NR—, —O—, —S—, —SO$_2$—, —COO—, —OOC—, —CONR—, —NRCO—, —SO$_2$NR—, —NRSO$_2$—, or terminated at the $R_f$ end with —CONR— or —SO$_2$NR—, where $R_f$ is attached to the carbon or sulfur atom, and where R is independently hydrogen, alkyl of 1 to 6 carbon atoms or hydroxyalkyl of 2 to 6 carbon atoms, and $R_f$ is a straight or branched chain perfluoroalkyl of 1 to 12 carbon atoms, perfluoroalkyl of 2 to 6 carbon atoms substituted by perfluoroalkoxy of 2 to 6 carbon atoms, or $R_f$ is an oligo(hexafluoropropene oxide) terminal group.

It is understood that the $R_f$ group usually represents a mixture of perfluoroalkyl moieties. When the $R_f$ group is identified as having a certain number of carbon atoms, said $R_f$ group also usually concomitantly contains a small fraction of perfluoroalkyl groups with a lower number of carbon atoms and a small fraction of perfluoroalkyl groups with a higher number of carbon atoms. Commonly the perfluoroalkyl moiety is a mixture of $C_4F_9$—, $C_6F_{13}$—, $C_8F_{17}$—, $C_{10}F_{21}$—, $C_{12}F_{25}$— and $C_{14}F_{29}$—.

Preferably the instant compounds are those where $R_f$ is perfluoroalkyl of 6 to 12 carbon atoms or perfluoroalkyl of 2 to 6 carbon atoms substituted by perfluoroalkoxy of 2 to 6 carbon atoms, E is alkylene of 2 to 6 carbon atoms, —CONHCH$_2$CH$_2$—, —CH$_2$CH$_2$N(CH$_3$)CH$_2$CH$_2$—, —CH$_2$CH$_2$SO$_2$NHCH$_2$CH$_2$— or —SO$_2$NHCH$_2$CH$_2$—.

Preferably $T_1$ is hydrogen or chloro.

Preferably $T_2$ is alkyl of 1 to 12 carbon atoms or phenylalkyl of 7 to 9 carbon atoms.

Most preferably $T_1$ is hydrogen.

Most preferably $T_2$ is alkyl of 1 to 8 carbon atoms or α,α-dimethylbenzyl.

Especially preferred, $T_2$ is methyl, tert-butyl, tert-amyl or tert-octyl.

Most preferred are those compounds where $R_f$ is perfluoroalkyl of 6 to 12 carbon atoms and E is ethylene.

Since the starting 2-(2-hydroxy-5-alkylphenyl)-2H-benzotriazole is already substituted in the para-position to the hydroxyl group, the Mannich base formation is perforce directed to the ortho-position to the hydroxyl moiety to obtain a 2-(2-hydroxy-3-dialkylaminomethyl-5-alkylphenyl)-2H-benzotriazole of formula II

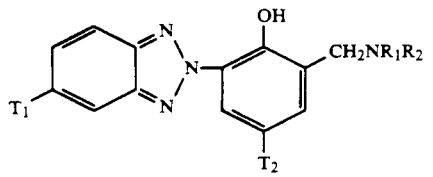

(II)

in which $T_1$ and $T_2$ are defined above, and $R_1$ and $R_2$ are independently alkyl of 1 to 6 carbon atoms.

The subject compounds are synthesized by first reacting the 2-(2-hydroxy-5-alkylphenyl)-2H-benzotriazole with an amine HNR$_1$R$_2$ and formaldehyde (or paraformaldehyde) in an organic solvent, such as butanol, to form the Mannich base. The base is converted to a hydrohalide or quaternary salt and then reacted with the desired fluorinated thiol in a high boiling inert solvent, such as p-cymene, or cumene. When reaction is complete the hot solution is filtered and the product precipitated quantitatively with alcohol.

Perfluoroalkyl thiols useful herein are well documented in the prior art. For example, thiols of the formula $R_f$—E—SH have been described inter alia U.S. Pat. Nos. 3,655,732 and 4,584,143.

Thus, U.S. Pat. No. 3,655,732 discloses mercaptans of formula $R_f$—E—SH where E is alkylene of 1 to 16 carbon atoms and $R_f$ is perfluoroalkyl, and teaches that halides of formula $R_f$—E-halide are well-known; the reaction of $R_f$I with ethylene under free-radical conditions gives $R_f(CH_2CH_2)_aI$ while reaction of $R_fCH_2I$ with ethylene gives $R_fCH_2(CH_2CH_2)_aI$ as is further taught in U.S. Pat. Nos. 3,088,849; 3,145,222; 2,965,659 and 2,972,638.

U.S. Pat. No. 3,655,732 further discloses compounds of formula $R_f$—R'—Y—R"—SH, where R' and R" are alkylene of 1 to 16 carbon atoms, with the sum of the carbon atoms of R' and R" being no greater than 25; $R_f$ is perfluoroalkyl of 4 through 14 carbon atoms and Y is —S— or —NR'"— where R'" is hydrogen or alkyl of 1 through 4 carbon atoms.

U.S. Pat. No. 3,544,663 teaches that the mercaptan $R_fCH_2CH_2SH$ where $R_f$ is perfluoroalkyl of 5 to 13 carbon atoms, can be prepared by reacting the perfluoroalkyl alkylene iodide with thiourea or by adding H$_2$S to a perfluoroalkyl substituted ethylene ($R_f$—CH=CH$_2$), which in turn can be prepared by dehydrohalogenation of the halide $R_f$—CH$_2$CH$_2$-halide.

The reaction of the iodide $R_f$—E—I with thiourea followed by hydrolysis to obtain the mercaptan $R_f$—E—SH is the preferred synthetic route. The reaction is applicable to both linear and branched chain iodides.

Particularly preferred herein are the thiols of formula $R_fCH_2CH_2SH$, where $R_f$ is perfluoroalkyl of 6 to 12 carbon atoms. These $R_f$-thiols can be prepared from $R_fCH_2CH_2I$ and thiourea in very high yield.

The subject 2-(2-hydroxy-3-perfluoroalkylthiomethyl-5-alkylphenyl)-2H-benzotriazoles are useful in stabilizing polymers by adsorption at the polymer/air interface even when used at very low concentration levels. The fluorinated additive molecules are sufficiently mobile in a solid polymer to reach and protect the surface by diffusion and selective adsorption. Thus, they have the unique ability to migrate to and stabilize an additive deficient surface.

The instant compounds inherently retain these unique migrating properties while being at a sufficiently high molecular weight necessary to minimize volatility. Therefore they can protect light-sensitive organic compositions from deterioration, especially at elevated temperatures.

This invention also relates to compositions stabilized against the deleterious effects of actinic light which comprises (a) an organic material subject to light-induced deterioration, and (b) an effective stabilizing amount of a compound of formula I.

The instant invention also pertains to a process for preparing the compounds of formula

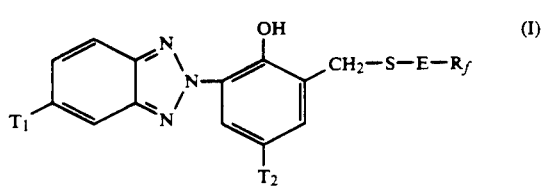

(I)

by reacting a compound of formula III

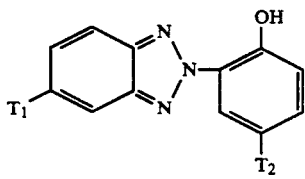

with an amine of formula $NHR_1R_2$ and formaldehyde to form a Mannich base of formula II

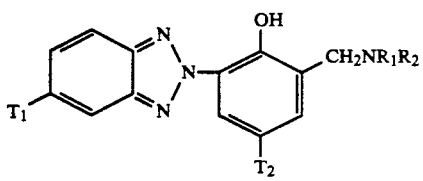

which is then converted to a hydrohalide or quaternary salt and reacted with a mercaptan of formula $R_f$—E—SH to give the compound of formula I, where $T_1$, $T_2$, E, $R_f$, $R_1$ and $R_2$ are as defined above.

The instant compounds exhibit good resistance to volatilization, enhanced solubility in selected solvents, desirable ultra-violet absorption characteristics, and photographic inertness. This combination of properties makes these benzotriazoles particularly useful in photographic compositions especially in protecting color dye images against the harmful effects of ultraviolet light.

The instant perfluoroalkyl substituted 2H-benzotriazoles are extremely useful as ultraviolet absorbers in photographic gelatin layers. They exhibit desirable adsorption characteristics in the ultraviolet region, i.e., maximum absorption in the near ultraviolet and sharp cut-off just outside the visible region, are essentially colorless, are readily dispersed or dissolved by either solvent-dispersion or imbibition methods, and are photographically inert.

The instant compounds exhibit excellent compatibility characteristics in the gelatin layers of the photographic composition which lead to compositions essentially without haze coupled with superior protection of the color dye images against the harmful effects of ultraviolet radiation. This combination of proper-ties clearly distinguishes the instant benzotriazole light absorbers.

Useful results are obtained when the instant benzotriazoles are incorporated directly into the gelatin layer or by the solvent dispersion technique.

An object of the invention is to provide novel photographic elements protected against the harmful effects of ultraviolet radiation by incorporation of ultraviolet absorbing materials. Another object is to provide photographic color materials containing ultraviolet absorbers incorporated in a highly stable form. A further object is to provide a non-diffusing ultraviolet absorber.

The invention relates further to stabilized organic material which is in the form of photographic material or is part of a photographic material, the photographic material containing, preferably in top layers, 0.05 to 5% by weight, relative to the photographic material without stabilizer, of a compound according to the invention.

In general polymers which can be stabilized include:
1. Olefins and diolefins, for example, polyethylene (which may be crosslinked), polypropylene, polyisobutylene, polybutene-1, polymethylpentene-1, polyisoprene or polybutadiene, as well as polymers of cycloolefins, for instance of cyclopentene or norbomene.

2. Mixtures of the polymers mentioned under 1., for example mixtures of polypropylene with polyisobutylene.

3. Copolymers of monoolefins and diolefins with each other or with other vinyl monomers, such as, for example, ethylene/propylene, propylene/butene-1, propylene/ isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbomene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer, and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5., for instance the copolymer mixtures known as ABS-, MBS-, ASA- or AES- polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinylchloride/vinylidene chloride, vinyl chloride/vinyl acetate, vinylidene chloride/vinyl acetate copolymers, or vinyl fluoride/vinyl ether copolymers.

8. Polymers which are derived from (alpha,beta-unsaturated acids and derivatives thereof, such as polyacrylates and polymethacrylates, polyacrylamide and polyacrylonitrile.

9. Copolymers from the monomers mentioned under 8. with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from bis-diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol and polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and nondrying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, for example, natural latex or lances of carboxylated styrene/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acrylic copolymers with pendant unsaturated groups and the acrylated melamines. The polyketimines are prepared from polyamines and ketones in the presence of an acid catalyst.

32. Radiation curable compositions containing unsaturated monomers or oligomers and a polyunsaturated aliphatic oligomer.

33. Epoxymelamine resins such as light-stable epoxy resins crosslinked by an epoxy functional co-etherified high solids melamine resin such as LSE4103 (Monsanto).

In general, the compounds of the present invention are employed from about 0.01 to about 5% by weight of the stabilized composition, although this will vary with the particular substrate and application. An advantageous range is from about 0.5 to about 2%, and especially 0.1 to about 1%.

The stabilizers can be blended before polymerization or during the usual polymer processing operations, for example, by hot-milling. The composition then being extruded, pressed, or the like into films, fibers, filaments, hollow spheres and the like.

The heat stabilizing properties of these compounds advantageously stabilize the polymer against degradation during such processing at the high temperature generally encountered. The stabilizers can also be dissolved in suitable solvents and sprayed on the surface of films, fabrics, filaments or the like to provide effective stabilization.

The stabilizer may be mixed with the polymer in dry powder form, or a suspension or emulsion of the stabilizer maybe mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

The stabilizers can also be added to the substrates to be stabilized in the form of a master batch which contains these compounds, for example in a concentration of 2.5 to 25% by weight.

When the substrate is a lubricating oil, said lubricating oil may be a mineral oil, a synthetic oil or any mixture of such oils. Mineral oils are preferred and examples of these include paraffinic hydrocarbon oils e.g. a mineral oil having a viscosity of 46 mm$^2$/s at 40° C.; "150 Solvent Neutral" a solvent refined neutral mineral oil having a viscosity of 32 mm$^2$/s at 40° C.; and "solvent bright-stocks", a high boiling residue from the process of refining mineral oil, and having a viscosity of 46 mm²/s at 40° C.

Synthetic lubricating oils which may be present may be synthetic hydrocarbons such as polybutenes, alkyl benzenes and poly-alpha olefins as well as simple di-, tri- and tetra-esters, complex esters and polyesters derived from carboxylic acid esters of formula: $G_1$—OCC-alkylene-COO$G_2$ wherein "alkylene" denotes an alkylene residue having from 2 to 14 carbon atoms and $G_1$ and $G_2$ are the same or different and each is an alkyl group having from 6 to 18 carbon atoms. Triesters which are of use as lubricating oil base stocks are those derived from trimethylolpropane and $C_6$–$C_{18}$ mono-carboxylic acids or mixtures thereof, whereas suitable tetra-esters include those derived from pentaerythritol and a $C_6$–$C_{18}$ mono-carboxylic acid or mixtures thereof Complex esters suitable for use as components of the composition of the present invention are those derived from monobasic acids, dibasic acids and polyhydric alcohols, for instance the complex ester derived from trimethylolpropane, caprylic acid and sebacic acid.

Suitable polyesters are those derived from any aliphatic dicarboxylic acid having from 4 to 14 carbon atoms and at least one aliphatic dihydric alcohol having from 3 to 12 carbon atoms, e.g. those derived from azelaic acid or sebacic acid and 2,2,4-trimethylhexane-1,6-diol.

Other lubricating oils are those known to the art-skilled and described e.g. in Schewe-Kobek, "Schmiennittel-Taschenbuch", (Huethig Verlag, Heidelberg 1974), and in D. Klamann, "Schmierstoff und verwandte Produkte", (Verlag Chemie, Weinheim 1982).

The lubricating oils applicational media can also contain other additives which may be added to improve the basic properties of lubricants e.g. metal passivators, viscosity-index improvers, pour-point depressants, dispersing agents, detergents, additional rust inhibitors, extreme pressure additives, anti-wear additives and antioxidants.

EXAMPLES OF PHENOLIC ANTIOXIDANTS

1. Alkylated Monophenols 2,6-Di-tert-butyl-4-methylphenol, 2,6-di-tert-butylphenol, 2-tert-butyl-4,6-dimethyl-phenol, 2,6-di-tert-butyl-4-ethyl-phenol, 2,6-di-tert-butyl-4-n-butylphenol, 2,6-di-tert-butyl-4-i-butylphenol, 2,6-di-cyclopentyl-4-methylphenol, 2-(β-methylcyclohexyl)-4,6-dimethylphenol, 2,6-di-octa-decyl-4-methylphenol, 2,4,6-tricyclohexylphenol, 2,6-di-tert-butyl-4-methoxymethylphenol, o-tert-butylphenol.

2. Alkylated Hydroquinones 2,6-Di-tert-butyl-4-methoxyphenol, 2,5-di-tert-butyl-hydroquinone, 2,5-di-tert-amyl-hydroquinone, 2,6-diphenyl-4-octadecyloxyphenol.

3. Hydroxylated Thiodiphenylethers 2,2'-Thio-bis-(6-tert-butyl-4-methylphenol), 2,2'-thio-bis-(4-octyl-phenyl), 4,4'-thio-bis-(6-tert-butyl-3-methylphenol), 4,4'-thio-bis-(6-tert-butyl-2-methylphenol).

4. Alkylidene-Bisphenols 2,2'-Methylene-bis-(6-tert-butyl-4-methylphenol), 2,2'-methylene-bis-(6-tert-butyl-4-ethylphenol), 2,2'-methylene-bis-(4-methyl-6-(α-methyl-cyclohexyl)-phenol), 2,2'-methylene-bis-(4-methyl-6-cyclohexylphenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-tert-butyl-4- or -5-isobutylphenol), 2,2'-methylene-bis-(6-(α-methylbenzyl-4-nonylphenol), 2,2'-methylene-bis-(6-(α,α-di-methylbenzyl)-4-nonylphenol), 4,4'-methylene-bis-(2,6-di-tert-butyl-phenol), 4,4'-methylene-bis-(6-tert-butyl-2-methylphenol), 1,1-bis-(5-tert-butyl-4-hydroxy-2-methyl-phenol)-butane 2,6-di-(3-tert-butyl-5-methyl-2-hydroxy-benzyl)-4-methyl-phenol, 1,1,3-tris-(5-tert-butyl-4-hydroxy-2-methyl-phenyl)-3-n-dodecyl)-mercaptobutane, ethyleneglycol-bis-[3,3-bis-(3'-tert-butyl-4'-hydroxyphenyl)-butyrate], bis-(3-tert-butyl-4-hydroxy-5-methylphenyl)-dicyclopentadiene, bis-[2-(3'-tert-butyl-2'-hydroxy-5'-methyl-benzyl)-6-tert-butyl-4-methyl-phenyl]-terephthalate.

5. Benzyl Compounds 1,3,5-Tri-(3,5-di-tert-butyl-4-hydroxybenzyl)-2,4,6-trimethyl-benzene, bis(3,5-di-tert-butyl-4-hydroxybenzyl)-sulfide, 3,5-di-tert-butyl-4-hydroxybenzyl-mercaptoacetic acid-isooctylester, bis-(4-tert-butyl-3-hydroxy-2,6-dimethyl-benzyl)dithiolterephthalate, 1,3,5-tris-(3,5-di-tert-butyl-4-hydroxybenzyl)-isocyanurate, 1,3,5-tris-(4-tert-butyl-3-hydroxy-2,6-dimethylbenzyl)-isocyanurate, 3,5-di-tert-butyl-4-hydroxybenzyl-phosphonic acid-dioctadecylester, 3,5-di-tert-butyl-4-hydroxybenzyl-phosphonic acid-monoethylester, calcium-salt.

6. Acylaminophenols

4-Hydroxy-lauric acid anilide, 4-hydroxy-stearic acid anilide, 2,4-bis-octyl-mercapto-6-(3,5-di-tert-butyl-4-hydroxyanilino)-s-triazine, N-(3,5-di-tert-butyl-4-hydroxyphenyl)-carbamic acid octyl ester.

7. Esters of β-(3,5-Di-tert-butyl-4-hydroxyphenyl)-propionic acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, tris-hydroxyethyl isocyanurate, thiodiethylene glycol, bis-hydroxyethyl oxalic acid diamide.

8. Esters of β-(5-tert-butyl-4-hydroxy-3-methylphenyl)-propionic acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, tris-hydroxyethyl isocyanurate, thiodiethylene glycol, di-hydroxyethyl oxalic acid diamide.

9. Amides of β-(3,5-Di-tert-butyl-4-hydroxyphenyl)-propionic acid for example N,N'-Bis-(3,5-di-tert-butyl-4-hydroxyphenylpropionyl)-hexamethylene-diamine, N,N'-bis-(3,5-di-tert-butyl-4-hydroxy-phenylpropionyl)-trimethylene-diamine, N,N'-bis(3,5-di-tert-butyl-4-hydroxyphenylpropionyl)-hydrazine.

EXAMPLES OF AMINE ANTIOXIDANTS

N,N'-Di-isopropyl-p-phenylenediamine, N,N'-di-sec.-butyl-p-phenylenediamine, N,N'-bis(1,4-dimethylpentyl)-p-phenylenediamine, N,N'-bis(1-ethyl-3-methyl-pentyl)-p-phenylenediamine, N,N'-bis(1-methyl-heptyl)-p-phenylenediamine, N,N'-dicyclohexyl-p- phenylenediamine, N,N'-diphenyl-p-phenylenediamine, N,N'-di-(naphthyl-2-)-p-phenylenedimnine, N-isopropyl-N'-phenyl-p-phenylenediamine, N-(1,3-dimethylbutyl)-N'-phenyl-p-phenylenediamine, N-(1-methylheptyl)-N'-phenyl-p-phenylene-diamine, N-cyclohexyl-N'-phenyl-p-phenylenediamine, 4-(p-toluene-sulfonamido)-diphenylamine, N,N'-dimethyl-N,N'-di-sec-butyl-p-phenylenediamine, di-phenylamine, N-allyldiphenylamine, 4-isopropoxy-diphenylamine, N-phenyl-1-naphthylamine, N-phenyl-2-naphthylamine, octylated diphenylamine, e.g. p,p'-di-tert-octyldiphenylamine, 4-n-butylaminophenol, 4-butyrylamino-phenol, 4-nonanoylamino-phenol, 4-dodecanoyl-amino-phenol, 4-octadecanoyl-amino-phenol, di-(4-methoxy-phenyl)-amine, 2,6-di-tert-butyl-4-dimethyl-amino-methyl-phenol, 2,4'-diamino-diphenylmethane, 4,4'-diaminodiphenyl-methane, N,N,N',N'-tetramethyl-4,4'-diamino-diphenylmethane, 1,2-di-(phenylamino)-ethane, 1,2-di-[2-methyl-phenyl)-amino]-ethane, 1,3-di-(phenylamino)-propane, (o-tolyl)-biguanide, di-[4-1',3'-dimethyl-butyl)-phenyl]amine, tert-octylated N-phenyl-1-naphthylamine, mixture of mono- and dialkylated tert-butyl-/tert-octyldiphenylamines, 2,3-dihydro-3,3-dimethyl-4H-1,4-benzothiazine, phenothiazine, N-allyl-phenothiazine, tert-octylated phenothiazine, 3,7-di-tert-octylphenothiazine.

EXAMPLES FOR OTHER ANTIOXIDANTS

Aliphatic or aromatic phosphites, esters of thiodipropionic acid or of thiodiacetic acid, or salts of dithiocarbamic or dithiophosphoric acid.

EXAMPLES OF METAL PASSIVATORS, FOR EXAMPLE FOR COPPER, ARE

Triazoles, benzotriazoles and derivatives thereof, tolutriazole and derivatives thereof, e.g. di(2-ethylhexyl)-aminomethyltolutriazole, 2-mercaptobenzothiazole, 5,5'-methylene-bis-benzotriazole, 4,5,6,7-tetrahydrobenzo-triazole, salicyclidene-propylene-diamine and salicyclamino-guanidine and salts thereof, 1,2,4-triazole and N,N'-disubstituted aminomethyl triazoles of formula

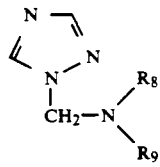

in which $R_8$ and $R_9$ are, independently, e.g. alkyl, alkenyl, or hydroxyethyl, obtained by reacting 1,2,4-triazole with formaldehyde and an amine, $HNR_8R_9$, as disclosed in European Patent Application No. 160620; and the Mannich reaction products derived from benzotriazole or tolutriazole, formaldehyde and an amine $HNR_8R_9$.

EXAMPLES OF RUST INHIBITORS ARE a) Organic acids, their esters, metal salts and anhydrides, e.g. N-oleoyl-sarcosine, sorbitan-mono-oleate, lead-naphthenate, alkenyl-succinic acids and -anhydrides, e.g. dodecenyl-succinic acid anhydride, succinic acid partial esters and amines, 4-nonyl-phenoxy-acetic acid.

b) Nitrogen-containing compounds, e.g.

I. Primary, secondary or tertiary aliphatic or cycloaliphatic amines and amine-salts of organic and inorganic acids, e.g. oil-soluble alkyl-ammonium carboxylates II. Heterocyclic compounds, e.g. substituted imidazolines and oxazolines.

c) Phosphorus-containing compounds, e.g. amine salts of phosphonic acid or phosphoric acid partial esters, zinc dialkyldithio phosphates.

d) Sulfur-containing compounds, e.g. barium-dinonylnaphthalene-n-sulfonates, calcium petroleum sulfonates.

e) Derivatives of gamma-alkoxypropylamines described in Japanese Patent Publication No. 15783/1973; and f) Salts having the formula $Y-NH_3-R_{10}CO_2-$ in which Y is a group $R_{11}X_1CH_2CH(OH)CH_2$ in which $R_{10}$ and $R_{11}$, independently, are e.g. alkyl and $X_1$ is O, $CO_2$, NH, N(alkyl), N(alkenyl) or S, these salts being prepared by mixing an amine $Y-NH_2$ with an acid $R_{10}CO_2H$, as disclosed in DE-OS 3437 876 (German Offenlegungsschrift).

g) Compounds having the formula

$$R_{12}-X_2-CH_2-CH(OH)-CH_2NR_{13}R_{14}$$

in which $X_2$ is $-O-$, $-S-$, $-SO_2-C(O)-O-$ or $-N(Rd)$ in which $R_{12}$ is H or $C_1-C_{12}$alkyl, $R_{13}$ is unsubstituted $C_1-C_4$alkyl or $C_2-C_5$alkyl substituted by one to three hydroxyl groups, $R_{14}$ is hydrogen, unsubstituted $C_1-C_4$alkyl or $C_2-C_5$alkyl substituted by one to three hydroxyl groups provided that at least one of $R_{13}$ and $R_{14}$ is hydroxy-substituted, and $R_{12}$ is $C_2-C_{20}$alkyl $-CH_2-CH(OH)-CH_2NR_{13}R_{14}$ or $R_{12}$ is $C_2-C_{18}$alkenyl, $C_2-C_3$alkynyl or $C_5-C_{12}$cycloalkyl provided that, when $X_2$ is $-O-$ or $-C(O)-O-$, $R_{12}$ is branched $C_4-C_{20}$alkyl. These compounds are described in GB Patent Specification 2172284A.

h) Compounds having the formula:

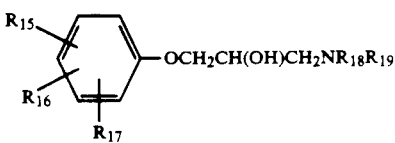

in which $R_{15}$, $R_{16}$, $R_{17}$ are, independently, hydrogen, $C_1-C_{15}$alkyl, $C_5-C_{12}$cycloalkyl, $C_6-C_{15}$aryl or $C_7-C_{12}$aralkyl and $R_{18}$ and $R_{19}$, independently, are hydrogen, 2-hydroxyethyl or 2-hydroxypropyl, provided that $R_{18}$ and $R_{19}$ are not simultaneously hydrogen and, when $R_{18}$ and $R_{19}$ are each $-CH_2CH_2OH$, $R_{15}$ and $R_{16}$ are not simultaneously hydrogen and $R_{17}$ is not pentyl. These compounds are described in EP Patent specification 0 252 007.

EXAMPLES OF VISCOSITY-INDEX IMPROVERS ARE

Polyacrylates, polymethacrylates, vinylpyrrolidone/methacrylate-copolymers, polyvinylpyrrolidones, polybutanes, olefin-copolymers, styrene/-acrylate-copolymers, polyethers.

EXAMPLES OF POUR-POINT DEPRESSANTS ARE

Polymethacrylates, alkylated naphthalene derivatives.

EXAMPLES OF DISPERSANTS/DETERGENTS ARE

Polybutenylsuccinic acid-amides or -amides, polybutenyl-phosphonic acid derivatives, basic magnesium-, calcium-, and bariumsulfonates and -phenolates.

EXAMPLES OF ANTI-WEAR ADDITIVES AND EXTREME PRESSURE ADDITIVES ARE

Sulphur- and/or phosphorus- and/or halogen-containing compounds e.g. sulphurised vegetable oils, zinc dialkyldithiophosphates, tritolylphosphate, chlorinated paraffins, alkyl- and aryldi- and trisulphides, triphenyl-phosphorothionate.

The following examples are presented for the purpose of illustration only and are not to be construed to limit the nature or scope of the instant invention in any manner whatsoever.

EXAMPLE 1

2-(2-Hydroxy-3-diethylaminomethyl-5-methylphenyl)-2H-benzotriazole 2-(2-Hydroxy-5-methylphenyl)-2H-benzotriazole (74.3 g, 0.33 mol), diethylamine (37.0 g, 0.51 mol) and paraformaldehyde (17.1 g) are dissolved in 85 mL of n-butanol. The mixture is heated with agitation at reflux (95° to 100° C.) for 44 hours. The solvent is removed by vacuum distillation, and the product, a yellow viscous liquid, is obtained in high yield (>99%). This Mannich base is identified by thin layer chromatography using toluene as the mobile phase.

EXAMPLE 2

2-(2-Hydroxy-3-diethylaminomethyl-5-tert-octylphenyl)-2H-benzotriazole 2-(2-Hydroxy-5-tert-octylphenyl)-2H-benzotriazole (70.0 g, 0.22 mol), diethylamine (24.3 g, 0.33 mol) and paraformaldehyde (11.2 g) are dissolved in 55 mL of n-butanol. The mixture is heated with agitation at reflux (95° to 100° C.) for 50 hours. The solvent is removed by a vacuum distillation, and the product, an off-white solid, is obtained in high yield (>99%). This Mannich base is identified by thin layer chromatography using toluene as the mobile phase.

EXAMPLE 3

2-(2-Hydroxy-3-(1,1,2,2-tetrahydroperfluorodecylthiomethyl)-5-methylphenyl)-2H-benzotriazole where $R_f$=5.0% $C_6F_{13}$; 94.0% $C_8F_{17}$; <1% $C_{10}F_{21}$ The product from Example 1 (31.0 g, 0.10 mol) is dissolved in p-cymene (75.0 g), and hydrogen chloride is bubbled through the solution to form the Mannich base hydrochloride. To the resulting slurry is added 1,1,2,2-tetrahydroperfluoro- decyl mercaptan (47.6 g, 0.10 mol). The mixture is heated with agitation, under nitrogen, at reflux (175° to 180° C.) for 20 hours. The reaction mixture is cooled to room temperature, thus precipitating the product. The product is filtered and triturated with hexane, yielding a white solid, 93% pure by GLC, m.p. 116°-118° C.

$^1$H NMR shows proton resonances at 2.38 ppm, 3 protons, (—C$\underline{H}_3$); 2.43 ppm, 2 protons, (—C$\underline{H}_2$R$_f$); 2.78 ppm, 2 protons, (—C$\underline{H}_2$CH$_2$R$_f$); 3.85 ppm, 2 protons, (—C$\underline{H}_2$S—); 7.18 ppm, 1 proton,(—SCH$_2$CCHCC-H$_3$—); 7.45 ppm, 2 protons, (2×—NCCHC$\underline{H}$—); 7.91 ppm, 2 protons, (2×—NCC$\underline{H}$CH—); 8.18 ppm, 1 proton, (—CH$_3$CC$\underline{H}$CN—); 11.60 ppm, 1 proton, (exchangeable OH proton).

Analysis: Calcd for $C_{24}H_{17}F_{17}N_3OS$: C, 40.2; H, 2.2; F, 45.0; N, 5.9. Found: C, 39.9; H, 2.0; F, 45.2; N, 5.7.

EXAMPLE 4

2-(2-Hydroxy-3-(1,1,2,2-tetrahydroperfluorooctylthiomethyl)-5-methylphenyl)-2H-benzotriazole where $R_f$=0.4% $C_4F_9$; 96.0% $C_6F_{13}$; 3.5% $C_8F_{17}$ The product from Example 1 (27.2 g, 0.088 mol) is dissolved in p-cymene (70.0 g) and hydrogen chloride is bubbled through the solution to form the Mannich base hydrochloride. To the resulting slurry is added 1,1,2,2-tetrahydroperfluorooctyl mercaptan (33.3 g, 0.088 mol). The mixture is heated with agitation, under nitrogen, at reflux (175° to 180° C.) for 24 hours. The reaction mixture is gravity filtered, and filtrate is cooled to room temperature and poured into cold (0° C.) methanol. The product crystallizes and is vacuum filtered, yielding 32.2 g of a white solid, 99% pure by GLC, m.p. 95°-97° C.

$^1$H NMR shows proton resonances at 2.38 ppm, 3 protons, (—C$\underline{H}_3$); 2.43 ppm, 2 protons, (—C$\underline{H}_2$Rf); 2.78 ppm, 2 protons, (—C$\underline{H}_2$CH$_2$Rf); 3.85 ppm, 2 protons, (—C$\underline{H}_2$S—); 7.18 ppm, 1 proton,(—SCH$_2$CCHCC-H$_3$—); 7.45 ppm, 2 protons, (2×—NCCHC$\underline{H}$—); 7.91 ppm, 2 protons, (2×—NCC$\underline{H}$CH—); 8.18 ppm, 1 proton, (—CH$_3$CC$\underline{H}$CN—); 11.60 ppm, 1 proton, (exchangeable OH proton).

Analysis: Calcd for $C_{22}H_{17}F_{13}N_3OS$: C, 42.7; H, 2.8; F, 39.9; N, 6.8; S, 5.2. Found: C, 42.7; H, 2.3; F, 39.2; N, 6.9; S, 5.6.

EXAMPLE 5

2-(2-Hydroxy-3-(1,1,2,2-tetrahydrofluoroalkylthiomethyl)-5-methylphenyl)-2H-benzotriazole where $R_f$=2.2% $C_4F_9$; 37.6% $C_6F_{13}$; 33.4% $C_8F_{17}$; 17.0% $C_{10}F_{21}$; 7.4% $C_{12}F_{25}$; 2.1% $C_{14}F_{29}$; 0.2% $C_{16}F_{33}$ The product from Example 1 (31.0 g, 0.10 mol) is dissolved in p-cymene (80.0 g), and hydrogen chloride is bubbled through the solution to form the Mannich base hydrochloride. To the resulting slurry is added 1,1,2,2-tetrahydroperfluoroalkyl mercaptan (47.6 g, 0.10 mol). The mixture is heated with agitation, under nitrogen, at reflux (175° to 180° C.) for 24 hours. The mixture is gravity filtered, and the filtrate is cooled to room temperature, and poured into cold (0° C.) methanol, thus precipitating the crystalline product. The product is filtered, yielding a pale yellow solid, 81% pure by GLC, m.p. 80°-110° C. The low purity is attributed to the presence of 14% the corresponding disulfide.

EXAMPLE 6

2-(2-Hydroxy-3-(1,1,2,2-tetrahydroperfluorodecylthiomethyl)-5-tert-octylphenyl)-2H-benzotriazole where $R_f$=5.0% $C_6F_{17}$; 94.0% $C_8F_{17}$; <1% $C_{10}F_{21}$;

The product from Example 2 (40.8 g, 0.10 mol) is dissolved in p-cymene (75.0 g), and hydrogen chloride is bubbled through the solution to form the Mannich base hydrochloride. To the resulting solution is added 1,1,2,2-tetrahydroperfluorodecyl mercaptan (47.6 g, 0.10 mol). The mixture is heated with agitation, under nitrogen, at reflux (175° to 180° C.) for 24 hours. The reaction mixture is gravity filtered, and the filtrate is cooled to room temperature and poured into cold (0°

C.) methanol, thus precipitating the crystalline product. The product is vacuum filtered, yielding 48.4 g of a pale yellow solid, 96% pure by GLC, m.p. 53°-60° C.

$^1$H NMR shows proton resonances at 0.80 ppm, 9 protons, (—C(CH$_3$)$_3$); 1.48 ppm, 6 protons, (—C(CH$_3$)$_2$); 1.83 ppm, 2 protons, (—CH$_2$C(CH$_3$)$_3$); 2.45 ppm, 2 protons, (—CH$_2$SR$_f$—); 7.38 ppm, 1 proton, (—SCH$_2$CCHC—); 2.75 protons, (—CH$_2$C(CH$_3$)$_3$); 3.98 ppm, 2 protons, (—CH$_2$S—); 7.50 ppm, 2 protons, (2×—NCCHCH—); 7.95 ppm, 2 protons, (2×—NCCHCH—); 8.38 ppm, 1 proton, (—CCH CN—); OH is not specifically observed.

Analysis: Calcd for C$_{31}$H$_{30}$F$_{17}$N$_3$OS: C, 45.6; H, 3.7; F, 39.6; N, 5.2. Found: C, 45.4; H, 3.5; F, 39.6; N, 5.1.

EXAMPLE 7

Thermogravimetric Analysis Data

In order to assess the resistance of the instant compounds to loss from a substrate by volatilization, representative samples of the compounds of formula I are exposed to thermogravimetric analysis.

The samples are exposed to isothermal conditions at 250° C. and also to conditions with a scanning rate of 10° C./minute. The results of these analyses are given in the table below.

| Stabilizer Compound of* | Isothermal at 250° C. Time (minutes) to indicated loss in weight of stabilizer | | Scanning at 10° C./min Temperature (°C.) to indicated loss in weight of stabilizer | |
|---|---|---|---|---|
| | 10% | 50% | 10% | 50% |
| UV I | 3.5 | 8.1 | 218 | 260 |
| UV II | 5.9 | 18.1 | 253 | 295 |
| Example 3 | 7.2 | 36.5 | 260 | 313 |
| Example 4 | 6.2 | 22.0 | 260 | 304 |
| Example 6 | 13.1 | 78.3 | 283 | 329 |

*UV I is 2-(2-hydroxy-5-methylphenyl)-2H-benzotriazole.
UV II is 2-(2-hydroxy-5-tert-octylphenyl)-2H-benzotriazole.

Inspection of these data clearly show that the instant compounds of formula I resist loss by volatilization even at very high temperatures better than do some 2-aryl-2H-benzotriazoles of the prior art.

EXAMPLE 8

Spectral Properties of R$_f$-Substituted 2H-Benzotriazole UV-Absorbers

The following table shows the absorption maxima and molar extinction coefficients of a number of 2H-benzotiiazole UV-absorbers. A state-of-the-art commercial benzotriazole UV-absorber, 2-[2-hydroxy-3,5-di-(α,α-dimethylbenzyl)phenyl]-2H-benzotriazole, and three instant R$_f$-substituted 2H-benzotriazole compounds are tested. The concentrations of each of the samples are identical, namely 20 mg/L.

| Absorption Maxima and Molar Extinction Coefficients of Benzotriazole UV Absorbers | | | | |
|---|---|---|---|---|
| Compound of | nm | Molar ε | nm | Molar ε |
| Control* | 302 | (15,200) | 342 | (15,500) |
| Example 3 | 304 | (13,777) | 340 | (15,191) |
| Example 4 | 304 | (15,293) | 340 | (16,483) |
| Example 6 | 303 | (16,333) | 340 | (15,554) |

*Control is 2-[2-hydroxy-3,5-di-(α,α-dimethylbenzyl)phenyl]-2H-benzotriazole.

The absorption properties of the R$_f$-substituted 2H-benzotriazoles are essentially the same as that of the commercial UV absorber control indicating that the instant R$_f$-substituted compounds would provide effective light stabilization protection to substrates from the deleterious effects of actinic light.

What is claimed is:

1. A composition stabilized against the deteriously effects of actinic light which comprises
   (a) an organic material subject to light-induced deterioration, and
   (b) an effective stabilizing amount of a compound of formula I

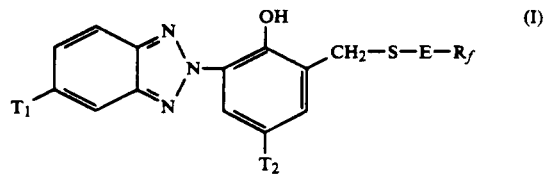

wherein

T$_1$ is hydrogen, halogen, alkyl of 1 to 4 carbon atoms or alkoxy of 1 to 4 carbon atoms, T$_2$ is alkyl of 1 to 18 carbon atoms, cycloalkyl of 5 to 12 carbon atoms or phenylalkyl of 7 to 15 carbon atoms, E is a branched or straight chain alkylene of 1 to 10 carbon atoms or said alkylene interrupted by one to three groups selected from the group consisting of —NR—, —O—, —S—, —SO$_2$—, —COO—, —OOC—, —CONR—, —NRCO—, —SO$_2$NR—, —NRSO$_2$—, or terminated at the R$_f$ end with —CONR— or —SO$_2$NR—, where R$_f$ is attached to the carbon or sulfur atom, and where R is independently hydrogen, alkyl of 1 to 6 carbon atoms or hydroxyalkyl of 2 to 6 carbon atoms, and R$_f$ is a straight or branched chain perfluoroalkyl of 1 to 12 carbon atoms, perfluoroalkyl of 2 to 6 carbon atoms substituted by perfluoroalkoxy of 2 to 6 carbon atoms, or R$_f$ is an oligo(hexafluoropropene oxide) terminal group.

2. A composition according to claim 1 wherein the organic material is an organic polymer.

3. A composition according to claim 2 wherein the organic polymer is a polyolefin.

4. A composition according to claim 3 wherein the polyolefin is polypropylene.

5. A composition according to claim 1 where in the compound of formula I, R$_f$ is perfluoroalkyl of 6 to 12 carbon atoms or perfluoroalkyl of 2 to 6 carbon atoms substituted by perfluoroalkoxy of 2 to 6 carbon atoms, E is alkylene of 2 to 6 carbon atoms, —CONHCH$_2$CH$_2$—, —CH$_2$CH$_2$N(CH$_3$)CH$_2$CH$_2$—, —CH$_2$CH$_2$SO$_2$NHCH$_2$CH$_2$— or —SO$_2$NHCH$_2$CH$_2$—.

6. A composition according to claim 1 where in the compound of formula I, T$_1$ is hydrogen or chloro.

7. A composition according to claim 6 wherein T$_1$ is hydrogen.

8. A composition according to claim 1 where in the compound of formula I, T$_2$ is alkyl of 1 to 12 carbon atoms or phenylalkyl of 7 to 9 carbon atoms.

9. A composition according to claim 8 wherein T$_2$ is alkyl of 1 to 8 carbon atoms or α,α-dimethylbenzyl.

10. A composition according to claim 8 wherein T$_2$ is methyl, tert-butyl, tert-amyl or tert-octyl.

11. A composition according to claim 1 where in the compound of formula I, R$_f$ is perfluoroalkyl of 6 to 12 carbon atoms and E is ethylene.

12. A composition according to claim 1 wherein the compound of component (b) is 2-(2-hydroxy-3-(1,1,2,2-tetrahydroperfluorodecylthiomethyl)-5-methylphenyl)-2H-benzotriazole;

2-(2-hydroxy-3-(1,1,2,2-tetrahydroperfluorooctylthiomethyl)-5-methylphenyl)-2H-benzotriazole; or 2-(2-hydroxy-3-(1,1,2,2-tetrahydroperfluorodecylthiomethyl)-5-tert-octylphenyl)-2H-benzotriazole.

13. A process for the preparation of a compound of formula I

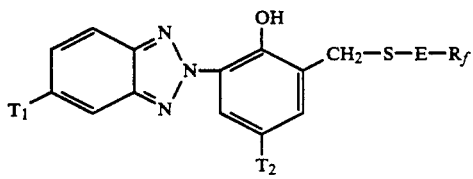
(I)

wherein $T_1$ is hydrogen, halogen, alkyl of 1 to 4 carbon atoms or alkoxy of 1 to 4 carbon atoms, $T_2$ is alkyl of 1 to 18 carbon atoms, cycloalkyl of 5 to 12 carbon atoms or phenylalkyl of 7 to 15 carbon atoms, E is a branched or straight chain alkylene of 1 to 10 carbon atoms or said alkylene interrupted by one to three groups selected from the group consisting of —NR—, —O—, —S—, —SO$_2$—, —COO—, —OOC—, —CONR—, —NRCO—, —SO$_2$NR—, —NRSO$_2$—, or terminated at the $R_f$ end with —CONR— or —SO$_2$NR—, where $R_f$ is attached to the carbon or sulfur atom, and where R is independently hydrogen, alkyl of 1 to 6 carbon atoms or hydroxyalkyl of 2 to 6 carbon atoms, and $R_f$ is a straight or branched chain perfluoroalkyl of 1 to 12 carbon atoms, perfluoroalkyl of 2 to 6 carbon atoms substituted by perfluoroalkoxy of 2 to 6 carbon atoms, or $R_f$ is an oligo(hexafluoropropene oxide) terminal group;

by reacting a compound of formula III

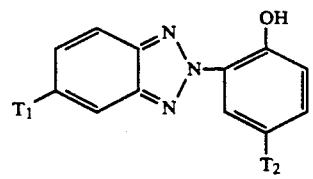
(III)

with an amine of formula $NHR_1R_2$ and formaldehyde to form a Mannich base of formula II

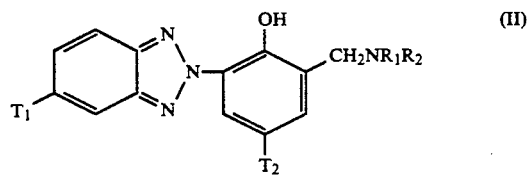
(II)

where $R_1$ and $R_2$ are independently alkyl of 1 to 6 carbon atoms, which is then converted to a hydrohalide or quaternary salt and reacted with a mercaptan of formula $R_f$—E—SH to give the compound of formula I, where $T_1$, $T_2$, E and $R_f$ are as defined above.

* * * * *